United States Patent [19]

Erlich

[11] Patent Number: 4,582,788

[45] Date of Patent: Apr. 15, 1986

[54] HLA TYPING METHOD AND CDNA PROBES USED THEREIN

[75] Inventor: Henry A. Erlich, Oakland, Calif.

[73] Assignee: Cetus Corporation, Emeryville, Calif.

[21] Appl. No.: 456,373

[22] Filed: Jan. 7, 1983

Related U.S. Application Data

[63] Continuation-in-part of Ser. No. 341,902, Jan. 22, 1982, abandoned.

[51] Int. Cl.$^4$ .................. C12Q 1/68; C12P 19/34; C12N 15/00; G01N 33/58
[52] U.S. Cl. .................................. 435/6; 435/91; 435/172.3; 436/504
[58] Field of Search ................ 435/6, 18, 19, 172.3, 435/91, 820, 948; 436/57, 183, 504, 530, 531

[56] References Cited

U.S. PATENT DOCUMENTS

| | | | |
|---|---|---|---|
| 4,394,443 | 7/1983 | Weissman et al. | 435/6 |
| 4,395,486 | 7/1983 | Wilson et al. | 435/6 |
| 4,471,056 | 9/1984 | Grumet et al. | 435/519 |
| 4,492,760 | 1/1985 | Defreitas | 436/503 |

FOREIGN PATENT DOCUMENTS 0103960 3/1984 European Pat. Off.
8303260 3/1982 PCT Int'l Appl.

OTHER PUBLICATIONS

Botstein et al., "Construction of a Genetic Linkage Map in Man Using Restriction Fragment Length Polymorphisms", American Journal of Human Genetics, 32, pp. 314–331 (1980).
Jordan et al., "Human HLA Gene Segment Isolated by Hybridization with Mouse H-2 cDNA Probes", Nature, 290, pp. 521–523 (1981).
Perkins, "The Human Major Histocompatibility Complex (MHC)", Basic and Clinical Immunology ed. Fundenberg et al., 1978, pp. 165–174.
Lee et al., "cDNA Clones Coding for the Heavy Chain of Human HLA-DR Antigen", Proceedings of the National Academy of Sciences, 79, pp. 545–549 (1–1982).
Sood et al., "Isolation and Partial Nucleotide Sequence of a cDNA Clone for Human Histocompatibility Antigen HLA-B . . . ", Proceedings of the National Academy of Sciences, 78(1), pp. 616–620 (1981).
Ploegh et al., "Molecular Cloning of a Human Histocompatibility Antigen cDNA Fragment", Proceedings of the National Academy of Sciences, 77(10), pp. 6051–6055 (1980).
Kan et al., "Polymorphism of DNA Sequence Adjacent to Human B-Globin Structural Gene: Relationship to Sickle Mutation", Proceedings of the National Academy of Sciences, 75(11), pp. 5631–5635 (1978).
Kan et al., "Polymorphism of DNA Sequence in the B-Globin Region", New England Journal of Medicine, 302(4), pp. 185–188 (Jan. 24, 1980).
Cosman et al., "Three Classes of Mouse H-2 Messenger RNA Distinguished by Analysis of cDNA Clones", Nature, 295, pp. 73–75 (1982).
B. Cami et al., Nature (1981) 291:673–675.
M. Steinmetz et al., Cell (1981) 24:125–134.
F. Brégégère et al., Nature (1981) 292:78–81.

Primary Examiner—Thomas G. Wiseman
Assistant Examiner—John E. Tarcza
Attorney, Agent, or Firm—Albert P. Halluin; Janet E. Hasak; Thomas E. Ciotti

[57] ABSTRACT

HLA typing based on restriction length polymorphism is carried out by: digesting an individual's HLA DNA with a restriction endonuclease that produces a polymorphic digestion pattern with HLA DNA; subjecting the digest to genomic blotting using a labeled cDNA hybridization probe that is complementary to an HLA DNA sequence involved in the polymorphism; and comparing the resulting genomic blotting pattern with a standard. This technique may be adapted to make paternity or transplant or transfusion compatibility determinations or to make disease association correlations to diagnose diseases or predict susceptibility to diseases. Locus specific cDNA hybridization probes, particularly probes for genes of Class II loci (D and DR loci), for use in the typing procedure are described.

9 Claims, 9 Drawing Figures

FIG_4.

HLA TYPING METHOD AND CDNA PROBES USED THEREIN

CROSS-REFERENCE TO RELATED APPLICATION

This application is a continuation-in-part of copending U.S. patent application Serial No. 341902 filed 22 Jan. 1982 now abandoned.

DESCRIPTION

1. Technical Field

The invention is in the fields of genetic engineering and human genotyping. More specifically the invention concerns methods for HLA typing based on HLA DNA restriction fragment length polymorphism and to novel complementary DNA (cDNA) probes that are used in such methods.

2. Background Art

The major histocompatibility complex (MHC) of humans is a cluster of genes occupying a region located on the sixth chromosome. This complex, denoted HLA (Human Leukocyte Antigen), has been divided into five major gene loci, which according to World Health Organization nomenclature are designated HLA-A, HLA-B, HLA-C, HLA-D, and HLA-DR. The A, B, and C loci are single gene loci. The D and DR loci are multi-gene loci. The A, B, and C loci encode the classical transplantation antigens, whereas the D and DR loci encode products that control immune responsiveness. More recent definitions divide the gene products of the HLA loci into three classes (I, II, and III) based on structure and function (Nature (1982) 297:692–632). Class I encompasses the products of the HLA-A, HLA-B, and HLA-C loci and the Qa/TL region. The products of the HLA-D and HLA-DR related genes fall in Class II. The Class II antigens are believed to be heterodimers composed of an $\alpha$ (~34,000 daltons) glycopeptide and a $\alpha$ (~29,000 daltons) glycopeptide. The number of loci and the gene order of Class II are tentative. Class II currently includes loci designated DR$\alpha$, DR$\beta$, DS$\beta$, DC($\alpha$ or $\beta$), and SB. It is likely that future investigation will reveal additional Class II loci. The third class, Class III, includes components of complement. As used herein, the term "HLA" is intended to include the above described loci as well as loci that are closely linked thereto.

The products encoded by the HLA loci are currently typed serologically or by mixed lymphocyte culture methods. Such typing is used in paternity determinations, transplant and transfusion compatibility testing, blood component therapy, anthropological studies and in disease association correlation to diagnose diseases or predict susceptibility to diseases. The major drawbacks to such HLA typing, particularly of the Class II loci, are the complexity of the sera and the lack of widespread availability of standard sera necessary to conduct the tests. Also, since serological typing is based on reactions of sera with the HLA gene products it may not be useful for fetal HLA typing in the early stages of pregnancy when those products have not yet been expressed. Further, the lymphocytotoxicity test often gives results that do not provide an adequate basis for recognizing Class II locus specificities.

It is well known that there is extensive polymorphism in the DNA of the human population. Recent work has also found polymorphism in the restriction endonuclease digests of human DNA. Restriction endonucleases recognize specific nucleotide sequences in DNA and catalyze endonucleolytic cleavages, yielding DNA fragments of defined length. Differences among individuals in the lengths of a particular restriction fragment are called "restriction fragment length polymorphisms" (RFLPs). Kan and Dozy, PNAS (1978) 75:5631–5635 report RFLPs produced by HpaI cleavage of human $\beta$-globin genes and an apparent association between a 13.0 kb variant of the normal 7.6 kb fragment and sickle hemoglobin mutation. These RFLPs were detected by comparing Southern blots of HpaI restricted cellular DNA from individuals with normal hemoglobin, sickle cell trait, and sickle cell anemia probed with a radiolabeled $\beta$-globin cDNA probe.

Botstein, et al, Am J Human Genet (1980) 32:314-331, have proposed using RFLPs as genetic markers to construct a genetic linkage map of the human genome. Their proposal contemplates identifying polymorphic loci by Southern blotting using restricted DNA and single strand cDNA probes, testing the loci for linkage relationships in human pedigrees, and arranging the loci into linkage groups to form a genetic map.

Sood, et al, PNAS (1981) 78:616–620 (also PCT application No. 8202060 published 24 June 1982), describe the isolation of cDNA clones for HLA-B antigens. These clones were prepared by synthesizing cDNA from an mRNA mix containing mRNA coding for the desired HLA antigen, inserting the cDNA into a vector, transforming a bacterial host and isolating transformant clones that contain the desired DNA segment by probing with an oligonucleotide probe that is specific for the desired DNA sequence. Ploegh, et al PNAS (1980) 77:6081–6085 have also reported cloning a cDNA probe for an HLA gene sequence.

DISCLOSURE OF THE INVENTION

One object of the invention is to provide a method of typing the HLA system based on HLA DNA restriction fragment length polymorphisms. Encompassed within this method are specific techniques of evaluating paternity and transplant or transfusion compatibility and for diagnosing disease susceptibility.

A second object of the invention is to provide novel HLA cDNA probes for use in the typing methods. Such probes include new locus specific probes, particularly for Class II loci.

The basic typing method comprises:

(a) digesting HLA DNA from an individual with a restriction endonuclease that produces a polymorphic digestion pattern with HLA DNA;

(b) subjecting the digest of (a) to genomic blotting using a labeled cDNA hybridization probe that is complementary to an HLA DNA sequence involved in the polymorphism; and (c) comparing the genomic blotting pattern obtained in (b) with a standard genomic blotting pattern for said HLA DNA sequence obtained using said restriction endonuclease and an equivalent labeled cDNA hybridization probe. As used in connection with describing the probe the term "equivalent" is intended to mean the same probe or one having the same specificity.

In an alternative embodiment of the invention the blotting step is replaced by a solution hybridization of the digest with the probe followed by resolution of the hybridizate. The resolution pattern is compared to a standard resolution for the HLA DNA sequence obtained using the same restriction endonuclease and an equivalent probe.

Identifying a specific HLA locus by this method involves using a restriction endonuclease that produces a polymorphic digestion pattern of the particular HLA locus and a cDNA hybridization probe that is specific to the HLA locus sequence.

As applied to paternity testing the method involves:

(a) digesting HLA DNA of the mother of the individual, the suspected father of the individual, and the individual with a restriction endonuclease that produces a polymorphic digestion pattern for HLA DNA;

(b) subjecting each of the digests of (a) to genomic blotting using a labeled cDNA hybridization probe that is complementary to an HLA DNA sequence involved in the polymorphism; and (c) comparing the genomic blotting patterns obtained in (b) to determine correspondence between the individual's pattern and the mother's and suspected father's pattern and thereby determining whether the suspected father is the actual father of the individual.

Use of the method for determining transplant or transfusion compatibility may be carried out in a manner similar to that used in paternity testing except that HLA DNA of the host and donor are analyzed and compared.

Use of the method in disease susceptibility prognosis involves comparing the individual's pattern with a standard pattern that is associated with the disease.

The novel cDNA hybridization probes of the invention are HLA locus specific. These locus specific probes comprise labeled DNA sequences that are complementary specifically to the DNA sequence in a given locus.

MODES FOR CARRYING OUT THE INVENTION

Figure 1:
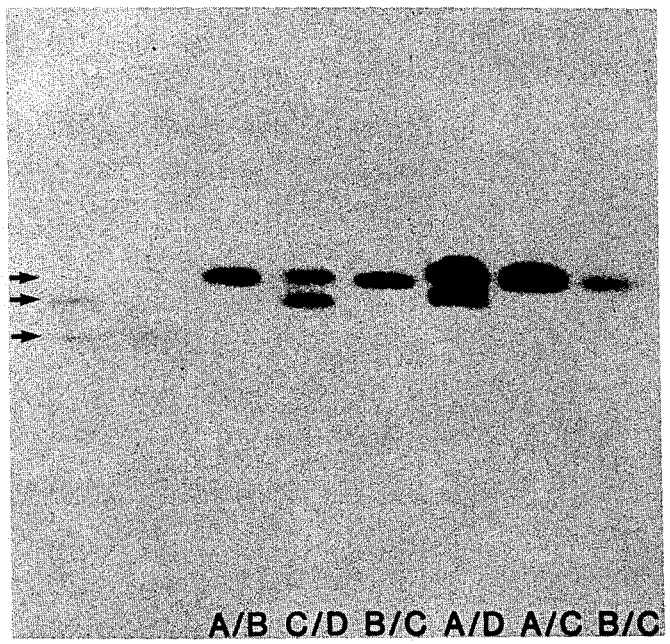
FIG. 1 is the autoradiograph described in Example 4.

The initial step in typing an individual's HLA by the invention method is to obtain a sample of the individual's HLA DNA. As used herein, the term "individual" is intended to include beings that are in a fetal stage. All nucleated cells contain HLA DNA and, therefore, are potential sources for the required DNA. For convenience peripheral blood cells will typically be used rather than tissue samples. As little as 10 to 100 cc of peripheral blood provide sufficient HLA DNA for typing. In the case of fetal HLA typing, placental cells or amniotic fluid may be used. The DNA is isolated from nucleated cells under conditions that preclude DNA degradation. Such isolation involves digesting the cells with a protease that does not attack DNA at a temperature and pH that reduces the likelihood of DNase activity followed by extraction of the digest with a DNA solvent. DNA isolation from nucleated cells is described by Kan, et al, *N Eng J Med* (1977) 297:1080–1084 and Nature (1974) 251:392–393, and Kan and Dozy, supra. The extracted DNA may be purified by dialysis, chromatography, or other known methods for purifying polynucleotides.

In the second step of the method the isolated DNA is restricted with a restriction endonuclease that cleaves or cuts DNA hydrolytically at a specific nucleotide sequence. Sequences so recognized by the enzymes are called restriction sites. Restriction endonucleases that recognize and cleave at specific sites are sometimes referred to as class II restriction enzymes (class I enzymes cleave randomly rather than at specific sites). Enzymes that produce blunt end DNA fragments (hydrolysis of the phosphodiester bonds on both DNA strands occur at the same site) as well as enzymes that produce sticky ended fragments (the hydrolysis sites on the strands are separated by a few nucleotides from each other) may be used. In any event, it is essential that the restriction endonuclease be one that produces a polymorphic digestion pattern associated with the HLA locus or loci under investigation. Determinations of which enzymes produce RFLPs at which loci may be made experimentally using various enzymes in conjunction with various specific HLA cDNA probes in the invention method. Table 1 lists the RFLPs that have been identified to date in this manner.

TABLE 1

| HLA cDNA probe | Enzymes revealing RFLP |
| --- | --- |
| pHLA-Dp34 (DRα) | BglII, EcoRV |
| p29G8 (DRα-related) | BglII |
| pHLA-B7 | EcoRI, PvuII, KpnI, XbaI, HindIII, BamH1 |
| pHLA-DRβ-4, (DRβ related) | EcoRI, BglII |
| pHLA-DRβ-8 | EcoRI, BglII |

The digestion of the DNA with the endonuclease may be carried out in an aqueous medium under conditions favoring endonuclease activity. Typically the medium is buffered to a pH of 6.5 to 8.0. Mild temperatures, 20° C. to 45° C., preferably physiological temperatures, are employed. Restriction endonucleases normally require magnesium ions and, in some instances cofactors (ATP and S-adenosyl methionine) or other agents for their activity. Therefore, a source of such ions, for instance inorganic magnesium salts, and other agents, when required, will be present in the medium. The amount of DNA in the digestion mixture will typically be in the range of 1% to 20% by weight. In most instances 5 to 20 μg of total cell DNA digested to completion provides an adequate sample for typing. Excess endonuclease, usually one to five units/ μg DNA, will be used. If desired the restriction digest may be worked up by precipitation and resuspension as described by Kan and Dozy, supra, prior to being subjected to genomic blotting or solution hybridization, as the case may be.

The third step of the process is analyzing the restriction digest by genomic blotting or solution hybridization and resolution for the presence of one or more HLA gene sequences. In the case of typing for a particular HLA gene the analysis is directed to detecting a DNA sequence that uniquely characterizes that gene. However, when the invention is used for paternity testing or transplant or transfusion compatibility the analysis does not necessarily involve identifying a specific locus or loci but may be done by comparing single or multilocus patterns of one individual with that of another individual using the same restriction endonuclease and an equivalent probe to determine similarities and differences between the patterns. In this regard a single locus probe will identify RFLPs associated with a single HLA locus whereas a multilocus probe will identify RFLPs associated with two or more HLA loci. Three basic steps are involved in the analysis: (1) resolving or separating the fragments by size; (2) annealing the fragments with a labeled cDNA probe that is complementary to the desired HLA DNA sequence(s); and (3) detecting the presence of labeled hybrids. The first two steps in the sequence—separating and annealing—are reversed in the solution hybridization embodiment. The genomic blotting embodiment uses the indicated sequence. The analysis method known as "Southern blotting" that is described by Southern, E.M. (1975) *J Mol Biol* 98:503-517 is currently a preferred analysis method. In Southern blotting the digestion products are electrophoresed, transferred and affixed to a support which binds nucleic acid, and hybridized with an appropriate labeled cDNA probe. Labeled hybrids are detected by autoradiography.

Electrophoresis is the separation of the digestion products contained in a supporting medium by size under the influence of an applied electric field. Gel sheets or slabs, eg agarose or agarose-acrylamide, are typically used as the supporting medium in Southern blotting. The electrophoresis conditions are such as to effect the desired degree of resolution of the fragments. A degree of resolution that separates fragments that differ in size from one another by as little as 100 base pairs will usually be sufficient. Size markers are run on the same gel to permit estimation of the size of the restriction fragments. In carrying out the electrophoresis, the digestion products are loaded onto one end of the gel slab (commonly called the "origin") and the fragments separate by electrically facilitated transport through the gel, with the shortest fragment electrophoresing from the origin towards the other (anode) end of the slab fastest.

After electrophoresis the gel is readied for annealing by placing it in a DNA denaturing solution, conveniently a mild base, generally about 0.2 to 1M hydroxide, preferably 0.5M NaOH, to dissociate the DNA strands. After denaturation, the gel is placed in a neutralizing solution and neutralized to a mildly acid pH. The DNA is then transferred to the substrate, which is typically made from materials such as nitrocellulose paper or diazobenzyloxymethyl paper, by contacting the gel with the paper in the presence of reagents, eg buffer, and under conditions, eg light weight and 0° C. to 25° C., that promote transfer and covalent or noncovalent binding of the DNA (particularly guanosine and uridine bases) to the sheets. Such reagents and conditions are described by Southern, E.M. supra, Wahl, et al, *PNAS* (1979) 6:3683-3687, Kan and Dozy, supra, and U.S. Pat. No. 4:302,204. After the transfer is complete the paper is separated from the gel and is dried. Hybridization (annealing) of the resolved single strand DNA on the paper to an HLA cDNA probe is effected by incubating the paper with the probe under hybridizing conditions. The hybridization will typically be conducted in an aqueous buffer solution containing a polar solvent such as formamide. Other additives that enhance the hybridization such as sodium chloride, sodium citrate, serum albumin and sonicated denatured DNA such as denatured salmon sperm DNA may be included in the hybridization medium. See Southern, supra, Kan and Dozy, supra and U.S. Pat. No. 4,302,204, col 5, line 8 et seq.

Complementary DNA probes that are specific to one (locus specific) or more (multilocus) particular HLA DNA sequences involved in the polymorphism are essential components of the hybridization step of the typing method. Locus specific cDNA probes may be made by identifying desired HLA cDNA clones in cDNA libraries constructed from membrane-bound mRNA using synthetic oligonucleotide probes that hybridize to specific HLA cDNA clones. The clones are made detectable by labeling them with a detectable atom, radical or ligand using known labeling techniques. Radiolabels, preferably $^{32}P$, will typically be used. The identified clones may be labeled with $^{32}P$ by nick translation with an $\alpha$-$^{32}P$-dNTP (Rigby, et al, *J Mol Biol* (1977) 113:237) or other available procedures to make the locus specific probes for use in the invention methods.

The base sequences for the synthetic oligonucleotide probes used to screen the cDNA libraries are determined from HLA antigen amino acid sequences using the genetic code. The amino acid sequences may be determined experimentally or from published data eg, Ploegh, et al, supra and Sood, et al, supra. Amino acids with minimal codon degeneracy are used whenever possible. If the amino acid sequence suggests more than one possible oligonucleotide sequence, all possible oligonucleotide sequences that code for the amino acid sequence are made and tested to determine which results in the best probe. Oligonucleotides having the desired base sequences may be prepared using the known phosphate diester, phosphate triester, or phosphite triester techniques. The phosphate triester method described by Good, et al, *Nucl Acid Res* (1977) 4:2157, is preferred. Blocked nucleotide reagents used in this method are available commercially. The specificity of a synthetic oligonucleotide may be determined by primer extension analysis or by using it as a hybridization probe in "Northern" blot analysis (a technique analogous to the Southern blot method for analyzing mRNA instead of DNA that was developed by Alwine, et al, *PNAS* (1977) 74:5350) of poly(A+) mRNA from a B cell line. Potential locus specific probes may also be identified by hybridizing cDNA library clones with multilocus probes and determining the specificity of the clones that anneal with the multilocus probes.

As more information about the DNA sequences of HLA genes becomes available it will be possible to discern whether there are any sequences that are unique to a particular locus, or perhaps a particular allele. Such information will permit the synthesis of locus specific probes that hybridize only to the unique portion of the gene. In this regard preliminary data have been developed indicating that in the case of the HLA-A and HLA-B loci the distinguishing portions of the genes may lie in the 3' untranslated regions.

The final step in the method is identifying labeled hybrids on the paper (or gel in the solution hybridization embodiment). Autoradiography is currently used to detect radiolabel-containing hybrids. It involves laying the paper on a piece of radiationsensitive film (X-ray film). The disintegration of the label results in the deposition of a silver grain in the film. The film is developed and the pattern of labeled fragments is identified. The specificity of the probe and the particular restriction endonuclease used will determine the number of fragments that appear in the pattern. Locus specific probes will typically give patterns with fewer bands than the patterns produced using multilocus probes.

As indicated previously these autoradiographs are used to determine HLA type or, in the case of paternity testing, transplant or transfusion compatibility, and disease association to determine similarities in the autoradiograph patterns of different individuals or similarities between an individual's pattern and a standard pattern, as the case may be. In this regard it will be appreciated that paternity testing and transplant or transfusion compatibility may also be carried out by HLA typing the individuals by the invention method and comparing their HLA types. In HLA typing the fragment(s) appearing on the test autoradiograph is/are compared to the fragment(s) that characterize a particular HLA type to determine correspondence therebetween and thus whether the test subject is that HLA type. This may be done by matching the test autoradiograph with a standard autoradiograph or simply matching the size distribution of the fragment(s) appearing on the test autoradiograph with the size distribution of fragment(s) for the standard. By evaluating the HLA DNA RFLP patterns for individuals of known (by conventional HLA typing) HLA type it is possible to assign specific restriction fragments to a given HLA locus. It is also expected that practice of the invention method will identify hitherto unidentified HLA genes, particularly in Class II. In this manner correlations between restriction fragment patterns and HLA type may and will be made. Such correlations may be used in deciphering test autoradiographs. The method also provides a technique for defining subdivisions of serologically defined HLA types. The use of HLA types in paternity tests, transplantation or transfusion testing and in disease diagnosis and prognosis is described in *Basic & Clinical Immunology*, 3rd Ed (1980) Lange Medical Publications, pp 187-190.

HLA cDNAs identified as potential probes may also be useful in making recombinant clones expressing human HLA antigens. In this connection, cDNA that encodes a given HLA antigen is inserted into an appropriate cloning vehicle (vector) and hosts are transformed with the vehicles. Transformants are isolated and those that produce the desired antigen are cloned. The antigen may be harvested from the clones by conventional methods. Such antigens may be useful for diagnostic purposes, for making anti-HLA antibodies, or for therapy to induce tolerance to HLA antigens.

The following examples further illustrate the various aspects of the invention. These examples are not intended to limit the invention in any manner.

EXAMPLE 1

Preparation of Hybridization Probe for HLA-Dp34 (HLA-DRα)

Four 11-mer oligonucleotides were prepared based on the known NH$_2$-terminal amino acid sequence (Glu, Phe, Tyr, Leu) of positions 11-14 of HLA-Dp34 antigen. The base sequences for the four oligonucleotides were as follows: (1) AGGTAAAATTC, (2) AGGTAGAATTC, (3) AGGTAAAACTC, and (4) AGGTAGAACTC. These sequences are all complementary to the codons for the indicated peptide sequence and were chosen to minimize degeneracy. The ambiguities are located at sequence positions 2, 3, 6, and 9. A G at positions 2 and 3 was chosen to minimize the destabilizing effect of potential mismatched bases (G is capable of forming a wobble pair with U).

Since the four oligonucleotides were complementary to codons for amino acids 11-14, oligonucleotide primed cDNA synthesis on HLA-Dp34 mRNA was expected to generate a product of about 150-200 nucleotides. This estimate was based on a leader sequence of ~75 nucleotides and assumes a 5' untranslated region of 75-125 nucleotides.

The specificities of the four 11-mers were compared by using them individually as primers in cDNA synthesis reactions using membrane-bound B cell mRNA, free B cell mRNA, and T cell mRNA as template. Only the AGGTAGAACTC oligonucleotide primed a cDNA band of ~175 nucleotides which was enriched in reactions on B cell membrane-bound mRNA template. The specificity of this 11-mer oligonucleotide was confirmed by extending the primer in a cDNA synthesis reaction in the presence of a single dideoxy triphosphate and three deoxy triphosphates, an approach which has proved successful in the isolation of the HLA-B7 cDNA clone (Sood, et al, supra). In the presence of dideoxy dATP, a minor cDNA band corresponding to a predicted 18-nucleotide primer extension product was observed. The additional seven nucleotides were determined by the wandering spot sequencing technique to be GGCCTGA. The following two additional nucleotides, AT, were inferred from the Ile codon, giving a nine nucleotide sequence that corresponded to the HLA-Dp34 antigen amino acids at positions 8, 9, and 10.

A 20-nucleotide fragment having the above determined sequence (AGGTAGAACTCGGCCTGAAT) was then synthesized by the triester method. The specificity of the 20-mer as a primer was examined in a cDNA synthesis reaction on poly(A+) mRNA from a B cell line. A major cDNA band, 175 nucleotides long, was synthesized; the nucleotide sequence of the eluted band, corresponded to the expected sequence for HLA-Dp34.

The specificity of the 20-nucleotide fragment as a hybridization probe was analyzed on a Northern blot of poly(A+) mRNA. A unique band, at 1200-1300 nucleotides resulted from probing B cell mRNA but not T cell mRNA with the $^{32}$P-labeled 20-mer nucleotide probe. Membrane-bound mRNA was enriched for the mRNA which hybridized to the 20-nucleotide probe.

An HLA-Dp34 cDNA clone was identified in a cDNA library with the above described 20-mer probe as follows. Membrane-bound RNA and free RNA was prepared, using phenol-chloroform extraction in the presence of Vanadyl complexes, from the human lymphoblastoid B cell line, CA. Poly(A+) mRNA isolated by affinity chromatography with Poly U-Sepharose, was translated in an in vitro rabbit reticulocyte system. The partition of specific mRNA's into the membrane-bound and free fractions was monitored by 2D gel analysis of the $^{35}$S-labeled products of in vitro translation. A double-stranded cDNA library was prepared from the membrane-bound mRNA using reverse transcriptase, DNA Polymerase I, and S1 nuclease. Following tailing with dCTP using terminal transferase, the cDNA was inserted and ligated to preparations of the plasmid pBR322 which had been digested with Pst and tailed with dGTP.

Initial screening of the library was carried out as follows. Duplicate sets (~4,000 clones/set) of Grunstein-Hogness colony filters were prepared. One set was probed with $^{32}$P cDNA made from size fractionated mRNA from the B cell line, CA. Sucrose gradient fractions were translated in an in vitro rabbit reticulocyte system and the $^{35}$S-labeled products analyzed by 2D gel electrophoresis to determine the appropriate fraction. The other set of filters was probed with $^{32}$ P cDNA made from mRNA from the T cell line, Molt-4. A subset of about 150 clones, derived from membrane-bound bound, B cell specific, 12–14s mRNA, was defined by this initial screening.

Plasmid DNA was prepared from 25 pools, each

18C7 clone to the mouse I region and therefore to the human HLA-D locus.

The 18C7 clone was confirmed as being HLA-Dp34 (HLA-DRα) by analyzing its DNA sequence by the Maxam-Gilbert technique (*Methods in Enzymology* (1980) 65:499–560) using the endonucleases PstI, HinfI, TaqI, Sau3A, AvaII, and BglII. The sequence for the coding strand of the HLA-Dp34 clone is given below (N =unidentified nucleotide).

| ATCATAGCTG | TGCTGATGAG | CGCTCAGGAA | TCATGGGCTA | TCAAAGAAGA |
|---|---|---|---|---|
| ACATGTGATC | ATCCAGGCCG | AGTTCTATCT | GAATCCTGAC | CAATCAGGCG |
| AGTTTATGTT | TGACTTTGAT | GGTGATGAGA | TTTTCCATGT | GGATATGGCA |
| AAGAAGGAGA | CGGTCTGGCG | GCTTGAAGAA | TTTGGACGAT | TTGCCAGCTT |
| TGAGGCTCAA | GGTGCATTGG | CCAACATAGC | TGTGGACAAA | GCCAACCTGG |
| AAATCATGAC | AAAGCGCTCC | AACTATACTC | CGATCACCAA | TGTACCTCCA |
| GAGGTAACTG | TGCTCACGAA | CAGCCCTGTG | GAACTGAGAG | AGCCCAACGT |
| CCTCATCTGT | TTCATCGACA | AGTTCACCCC | ACCAGTGGTC | AATGTCACGT |
| GGCTTCGAAA | TGGAAAACCT | GTCACCACAG | GAGTGTCAGA | GACAGTCTTC |
| CTGCCCAGGG | AAGACCACCT | TTTCCGCAAG | TTCCACTATC | TCCCCTTCCT |
| GCCCTCAACT | GAGGACGTTT | ACGACTGCAG | GGTGGAGCAC | TGNGGCTTGG |
| ATGAGCCTCT | TCTCAAGCAC | TGGGAGTTTG | ATGCTCCAAG | CCCTCTCCCA |
| GAGACTACAG | AGAACGTGGT | GTGTGCCCTG | GGCCTGACTG | TGGGTCTGGT |
| GGGCATCATT | ATTGGGACCA | TCTTCATCAT | CAAGGGAGTG | CGCAAAAGCA |
| ATGCAGCAGA | ACGCAGGGGG | CCTCTGTAAG | GCACATGGAG | GTGATGATGT |
| TTCTTAGAGA | GAAGATCACT | GAAGAAACTT | CTGCTTTAAT | GACTTTACAA |
| AGCTGGCAAT | ATTACAATCC | TTGACCTCAG | TGAAAGCAGT | CATCTTCAGC |
| GTTTTCCAGC | CCTATAGCCA | CCCCAAGTGT | GGTTATGCCT | CCTCGATTGC |
| TCCGTACTCT | AACATCTAGC | TGGCTTCCCT | GTCTATTGCC | TTTTCCTGTA |
| TCTATTTTCC | TCTATTTCCT | ATCATTTTAT | TATCACCATG | CAATGCCTCT |
| GGAATAAAAC | ATACAGGAGT | CTGTCTCTGC | TATGGAATGC | CCCATGGGGC |
| TCTCTTGTGT | ACTTATTGTT | TAAGGTTTCC | TCAAACTGTG | ATTTTTCTG | consisting of 5 candidate cDNA clones and analyzed by dot hybridization with the 32P-labeled 20-nucleotide probe. Pool 14 plasmid DNA hybridized specifically with the probe. Subsequently, the individual members of the pool were tested; cDNA sequences complementary to the hybridization probe were restricted to the clone identified as 18C7.

In Northern blots, the $^{32}$P-labeled 18C7 nick translated probe hybridizes to a B cell mRNA of the same length (about 1200 to about 1300 nucleotides) as the band complementary to the 20-nucleotide probe. In genomic blots with DNA from a hamster-human hybrid containing the human chromosomes 6 and 3, the 18C7 probe hybridizes to a unique restriction fragment absent in the hamster parent, mapping the 18C7 DNA sequences to chromosome 6.

A more precise mapping was possible using the cell line 6.3.6 which has a small deletion at a defined site on the short arm of one homologue of the chromosome 6 pair. This deletion variant fails to express the HLA-A, B, C and HLA-DR specificities associated with one chromosome 6 haplotype. In genomic blots (FIG. 1 and Example 4 below), 18C7 hybridizes to two restriction fragments from the parent cell line, presumably from the two chromosome 6's. Only one fragment is observed in DNA from the deletion variant; the other fragment is presumably derived from the chromosome which has been deleted. This result maps DNA sequences complementary to the 18C7 clone to the chromosomal site defined by the 6.3.6 deletion.

The human HLA-D locus is homologous to the mouse I region. In genomic blots with DNA from mouse congenic lines, inbred lines which differ only at the I region, the 18C7 probe hybridized to a restriction fragment that was different with each congenic line. This result maps DNA sequences complementary to the A$^{32}$P-labeled HLA-Dp34 probe was made from the clone by nick translation.

EXAMPLE 2

Preparation of Hybridization Probe for Ia Like Class II HLA p29G8

The HLA-DRα related or human Ia like clone, p29G8, was identified by screening the cDNA library of Example 1 with the nick-translated HLA-Dp34 (DRα) probe under hybridization conditions of reduced stringency to allow detection of related but distinct DNA sequences. The hybridization conditions were as follows.

Hybridize in 50% formamide, 5×SSPE (1×SSPE=0.18M NaCl, 10 mM NaH$_2$PO$_4$, 1 mM Na$_2$EDTA, pH 7.0), 0.1% sodium dodecyl sulfate (SDS), 5×Denhardt's (5×Denhardt's=0.1% w/v each bovine serum albumin, Ficoll, polyvinyl pyrollidone), 200 μg/ml sheared denatured salmon sperm DNA, at 37° C. for 24 h with 1×10$^6$ cpm $^{32}$ P labeled HLA Dp34 probe (2×10$^8$ cpm/μg, labeled by nick translation). Wash filters 3×15 min at room temperature in 5×SSPE, 0.1% SDS.

Fifteen HLA-DRα related cDNA clones were identified. Among them was a clone designated p29G8. Under conditions of high stringency (wash at 0.1×SSPE, 65° C.), p29G8 hybridizes strongly only to itself. The p29G8 clone (minus strand) was partially sequenced using the Maxam-Gilbert procedure. Four fragments, designated A1, A2, B1, and B2, were obtained by digesting the p29G8 clone. The clone was first digested with with PstI to yield a ~400 bp fragment and a ~600 bp fragment. The larger fragment was cut with Sau3A to give fragment A1 or with MspI to give fragment A2. The smaller fragment was cut with HaeIII to give fragment B1 or with Sau3A to give fragment B2. The sequences of these fragments are reported below (N=unidentified nucleotide).

Fragment A1
TNTGAACNCCAGCTGCCCTACAAACTCCATCTCAGCTTTTCTTCTCACTTCATG
TNAAAACTACTCCAGTGGCTGACTNAATTGCTGACCCTTCAAGCTCTGTCCTTA
TCCATTACCTCAAAGCAGTCATTCCTTAGTNAAGTTTCCAAC
Fragment A2
CACGGGAGNCCCAAGAGCCAACCAGACGCCTGAGACAACGGAGACTGTGCTCTG
TGCCCTGGGCCTGGTGCTGGGCCTAGTCGGCATCATCGTGGGCACCGTCCTNAT
CATAAAGTCTCTGCGTTCTGGCCATGACCCCC
Fragment B1
CACATTGACGAGTTCTTCCCACCAGTCCTCAANGTCACGTGGGCCGCGCAACGG
GGAGCTGGTCACTGAGGG
Fragment B2
AAGGAGACCGTCTGGCATCTGGAGGAGTTTGGCCAAGCCTTTTCCCTTTGAGGC
TCAGGGCGGGCTGGCTAACATTGCTATATTGAACAACAACTTGAAACCTTGA The partial sequence is distinct from the sequence for HLA-Dp34 (DRα) and differs from the recently published nucleotide sequence for the HLA-DC1 clone (Auffrey, et al, (1982) *PNAS* Vol 79:6637–6341) both in sequence and length of the 3' untranslated region. In genomic Southern blots, the p29G8 probe hybridizes to genomic restriction fragments distinct from those which hybridize to the HLA-Dp34 (DRα) probe in DNA from an HLA hemizygous cell line (6.3.6). This observation indicates that p29G8 represents a different (new) locus and not simply another allele. The genomic blot pattern with DNA from the cell line T5-1 and its HLA hemizygous derivative 6.3.6 indicates that the p29G8 locus maps within the HLA region.

EXAMPLE 3

Characterization of Other Class II HLA cDNA Clones

DRα

As indicated in Example 2, fourteen other DRα-related cDNA clones were identified. Four of these clones are very strongly homologous to the HLA-Dp34 Dp34 (DRα) clone and are probably identical or allelic copies. Thus, ten clones represent candidates for new HLA-DRα related loci. These ten clones are listed below.

| | |
|---|---|
| p14A9 | p11G7 |
| p17D8 | p36A1 |
| p22G12 | p51H2 |
| p40G4 | p25A6 |
| p6B3 | p36F7 |

Clone p14A9 hybridizes to genomic restriction fragments distinct from those that hybridize to the HLA-Dp34 (DRα) and p29G8 probes. Thus, p14A9 represents a third DRα related locus. By comparing the pattern of cross-hybridization of these HLA-DRα related clones, it was estimated that these 10 HLA-DRα related clones represent a minimum of two and a maximum of 10 different HLA-DRα related loci. DRβ

An 18-mer having the base sequence CCCTGTCTCGCGCACGCA was prepared for use in screening a cDNA library of HLA-DRβ clones. The sequence of the 18-mer was based on the published amino acid sequence for the conserved amino acids 20-25 of the HLA-DRβ chain. The specific 18-nucleotide sequence was chosen from the published sequence of an HLA-DRβ cDNA clone from the Raji cell line (Wiman et al (1982) *PNAS* 79:1703–1707). The specificity of the kinased 18-mer probe was tested by hybridization to an RNA blot. The probe hybridized to an RNA species about 1100–1300 nucleotides long present in B cell RNA and absent from T cell RNA, as expected for the HLA-DRβ mRNA. Hybridization conditions were for 36 h at 37° C. in 4×SSPE with 5×Denhardt's solution, 0.2 mM ethylene diaminewith tetraacetic acid (EDTA), and 0.1% SDS. Filters were washed in 2×SSPE, 0.1% SDS at room temperature.

The 18-mer probe was hybridized to a cDNA bank derived from mRNA from the β lymphoblastoid cell line, LG2. The cDNA bank was constructed by inserting the duplex cDNA ligated to EcoRI linkers into the EcoRI site of the λgt 10 vector. cDNA inserts from eight 18-mer reactive λ cDNA clones were isolated and subcloned into the EcoRI site of the plasmid vector, pBR328 (Soberon, X., et al, Gene (1980) 9:287-305). The clones designated DRβ-4 and DRβ-8 hybridize to sequences in the HLA region using the genomic blotting technique with the 6.3.6 HLA hemizygous deletion variant described in Example 1. The products of in vitro translation of mRNA which hybridize to DRβ chains have the electrophoretic mobility expected of HLA-DRβ chains. In oocytes, the translation products of specifically hybridizing mRNAs associate with the translation products of HLA-DRα and HLA-DRγ mRNAs. Thus by a variety of criteria, these clones encode HLA-DR, β or DRβ like proteins. The genomic blot patterns obtained with the HLA-DRβ-4 and HLA-DRβ-8 probes are different indicating these clones represent different loci.

EXAMPLE 4

Determination of HLA-DRα Restriction Fragment Length Polymorphism Using BglII and HLA-Dp34 Hybridization Probe Digestion of DNA with BglII Samples of DNA were obtained from nucleated cells of five unrelated individuals and four children of two of the individuals. Five to ten μg of each DNA sample were digested for 1-2 hr at 37° C. with 4(15') units of BglII per μg of DNA. The buffer was 60 mM NaCl, 6 mM Tris HCl (pH 7.5), 6 mM MgCl$_2$, 6 mM 2-mercaptoethanol.

Genomic Blotting of Restriction Digests with HLA-Dp34 Probe

Between five and ten μg of each restriction enzyme digested DNA was fractionated according to size by electrophoresis in a 0.6% agarose gel for approximately 500 V-hr. Eletrophoresis buffer was 40.0 mM Tris, 2.5 mM EDTA, 25.0 mM acetate, pH 8.2. After electrophoresis the DNA was stained with 0.5 μg/ml ethidium bromide and the gel was photographed. The DNA in the gel was depurinated with a 15' wash in 75 mM HCl at room temperature. DNA was denatured with 2 successive 15' washes in 0.5M NaOH +1.5M NaCl at room temperature. DNA was neutralized with 2 successive 15' washes in 1.5M Tris-Cl pH 7.4 +3.0M NaCl at room temperature. DNA was transferred from the gel to nitrocellulose (0.45 micron pore size) by blotting with 20×SSPE (20×SSPE =3.6M NaCl, 200.0 mM phosphate, 20.0 mM Na$_2$EDTA, pH 7.0) for 3 hr at room temperature. DNA was bound to the nitrocellulose by baking at 80° C. for 2 hr in a vacuum oven.

The nitrocellulose filter was placed in a heat sealable plastic bag and was prehybridized for 8 hr at 42° C. in a solution composed of 50% formamide, 5×SSPE, 200 μg/ml sheared denatured salmon sperm DNA, 0.1% SDS, and 2×Denhardt's solution. After 8 hr, the prehybridization solution was removed from the bag and replaced with a solution composed of 50% formamide, 5×SSPE, 100 μg/ml sheared denatured salmon sperm DNA, 0.1% SDS, 2×Denhardt's solution, 10% sodium dextran sulphate, and 1–5×10$^6$ cpm denatured $^{32}$P labelled HLA-Dp34 probe. The probe was labeled using the nick translation reaction of Rigby, et al, supra, to specific activities of $5 \times 10^8$–$1 \times 10^9$ cpm/μg. The bag was resealed and the nitrocellulose filter was hybridized with the probe for 18–24 hr at 42° C.

The nitrocellulose filter was removed from the bag and washed in 4 successive changes (15' each) of 2×SSPE, 0.17% SDS at room temperature. The filter was then washed in 4 successive changes (15' each) of 0.1×SSPE, 0.1% SDS at 50° C.

The filter was air dried, covered with Saran Wrap and autoradiographed with Kodak XAR-5 film with an intensifying screen for 18–72 hr at −80° C. FIG. 1 is a copy of the resulting autoradiograph.

Discussion of Autoradiograph

The autoradiograph shows that BglII produced three different restriction fragments in the tests: 3.8, 4.2, and 4.5 kb in length. This clearly evidences that the HLA-Dp34 locus is polymorphic and that there are at least three alleles of this gene.

Lane 1 of the autoradiograph is a blot of the cell line CA. Lanes 3 and 2 of the autoradiograph are blots of the cell line 6.3.6 and its parent T5-1, respectively. These are the blots discussed in Example 1 that map the HLA-Dp34 gene to chromosome 6 at the site defined by the 6.3.6 deletion.

Lanes 4 and 5 are blots of the mother and father of a family and lanes 6–9 are blots of the children of those parents. Lane 4 is the father's blot and his haplotype is designated A/B. Both chromosome A and chromosome B have the same restriction fragment (4.2 kb). Lane 5 is the mother's blot and her haplotype is designated C/D. Each chromosome C and D has a different restriction fragment (4.2 kb and 4.5 kb, respectively). In the offspring of these parents the maternal 4.2 kb genomic fragment segregates with the serologically defined D haplotype.

EXAMPLE 5

HLA-Dp34 Typing Based on RFLP Using HLA-Dp34 Hybridization Probe and the Restriction Endonuclease BglII A sample of peripheral blood is obtained from an individual and the HLA DNA is extracted therefrom using the methods described in Example 4. The DNA is digested using BglII and a genomic blot of the digest is made using the HLA-Dp34 as described in Example 4. The restriction fragment pattern of the resulting autoradiograph is compared to the restriction fragment patterns described in Example 4 (FIG. 1) for HLA-Dp34 to determine the individual's HLA-Dp34 type.

EXAMPLE 6

Figure 2:
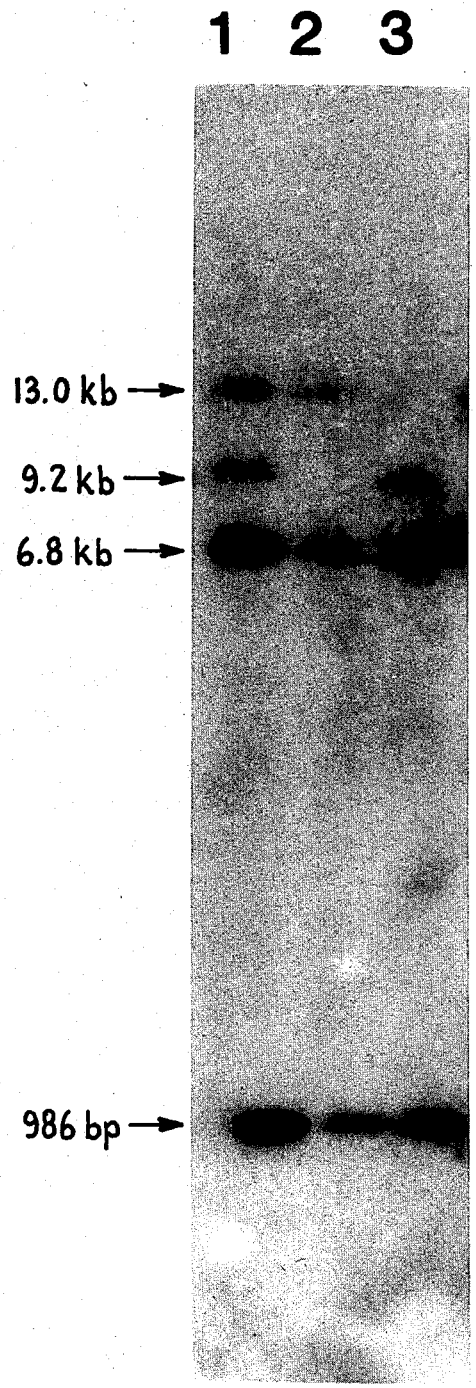
FIG. 2 is the autoradiograph described in Example 6.

Restriction Fragment Length Polymorphisms Detected with EcoRV and HLA-Dp34 (DRα) Probe Ten μg samples of DNA were obtained from three individuals and digested for 1–4 hr at 37° C. with 80 units of EcoRV. The buffer was 0.15M NaCl, 6 mM Tris HCl (pH 7.9), 6 mM MgCl$_2$, 6 mM 2-mercaptoethanol. Genomic blotting and hybridization of restriction digested DNAs were carried out as in Example 4. An autoradiograph was prepared of the genomic blotting patterns as in Example 4. FIG. 2 is a copy of the resulting autoradiograph.

Figure 3:
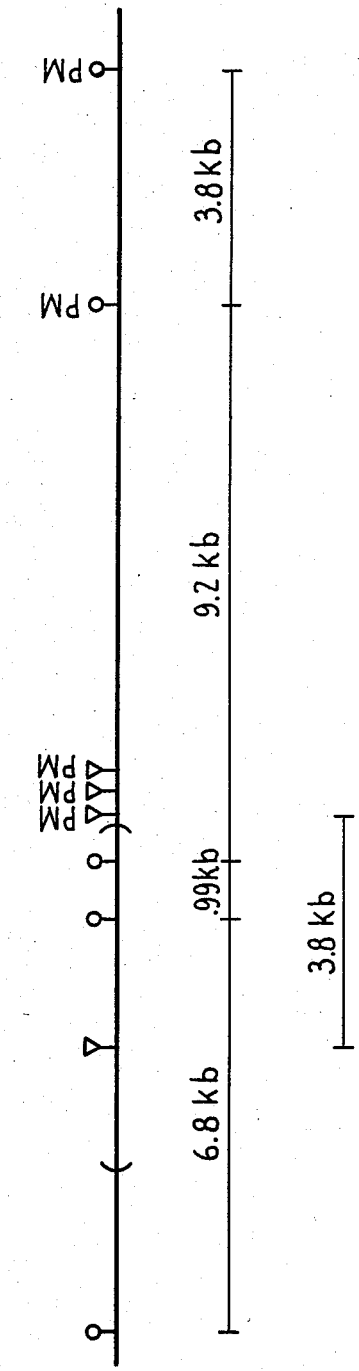
FIG. 3 is a restriction map of the HLA-DR α locus showing the location of polymorphic restriction sites for the enzymes BglII and EcoRV detected with the probe of Example 1.

As seen in FIG. 2, all three individuals possess a 986 bp and a 6.8 kb EcoRV fragment (nonpolymorphic fragments). In addition, every individual possesses either a 9.2 kb or a 13.0 kb EcoRV fragment, or both (polymorphic fragments). FIG. 3 is a map diagramming the location of the polymorphic restriction sites for BglII (Example 4) and EcoRV detected with the HLA-Dp34 probe.

EXAMPLE 7

Determination of Restriction Fragment Length Polymorphism in Class II Locus Using BglII and Hybridization Probe p29G8

Figure 4:
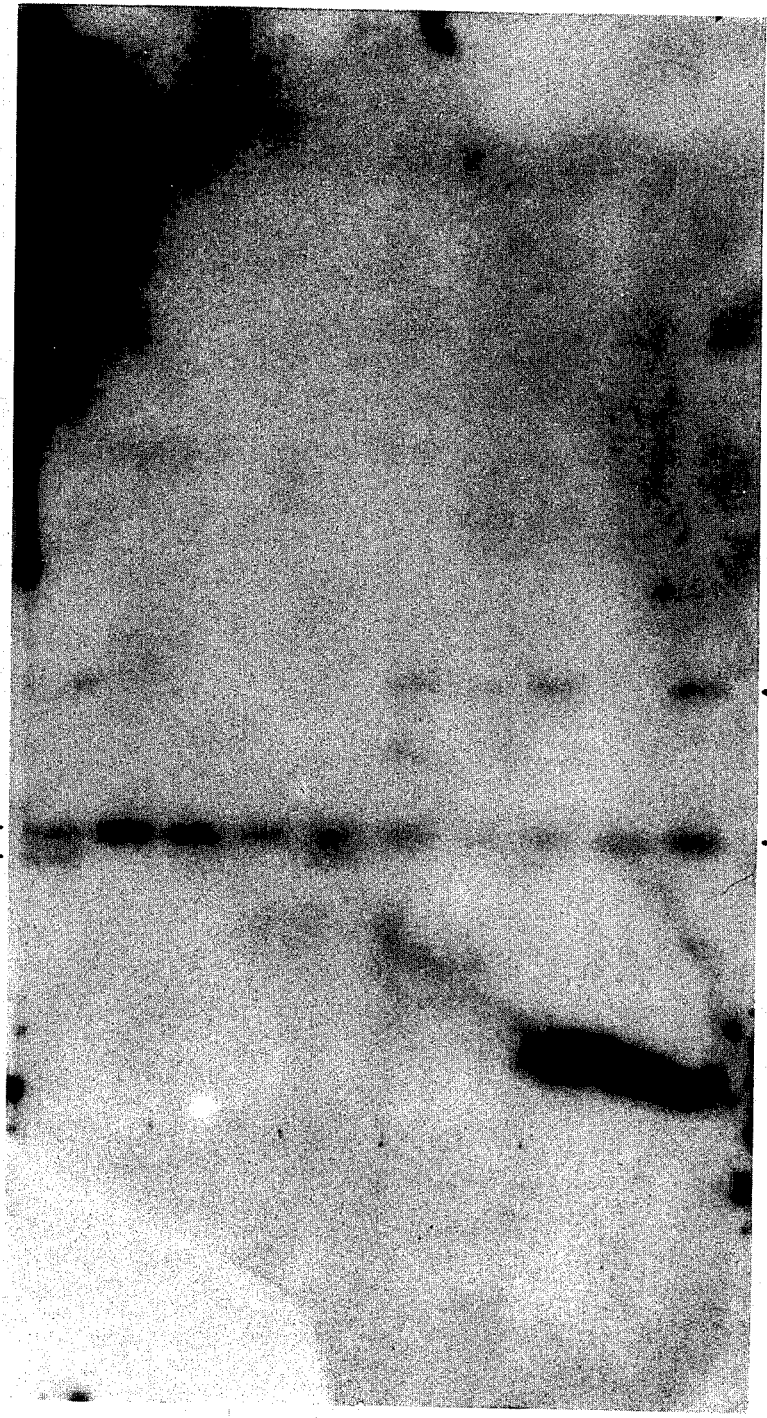
FIG. 4 is the autoradiograph described in Example 7.

Ten μg samples of DNA from five individuals of one family and five individuals of a second family were digested with BglII using the procedure of Example 4. The digests were subjected to electrophoresis, genomic blotting and hybridization by the procedure of Example 4 except that the nick translated p29G8 probe of Example 2 was used instead of the HLA-Dp34 probe. FIG. 4 is an autoradiograph of the resulting genomic blotting patterns. Lanes 1–5 are the patterns for the five individuals of the first family and Lanes 6–10 are the patterns of the five individuals of the second family. As seen in FIG. 4 three types ("alleles") were observed in the samples characterized by 2.2 kb, 2.4 kb, and 4.4 kb fragments. In the HLA typed families of this example the polymorphic BglII fragments segregate with serologically defined parental haplotypes.

EXAMPLE 8

Use of HLA-B7 Hybridization Probe to Evaluate HLA Restriction Fragment Length Polymorphisms in Human Pedigrees An HLA-B7 cDNA clone was obtained from Sherman M. Weissman, Dept of Human Genetics, Yale University School of Medicine. This clone is described in Sood, et al, supra.

Figure 5:
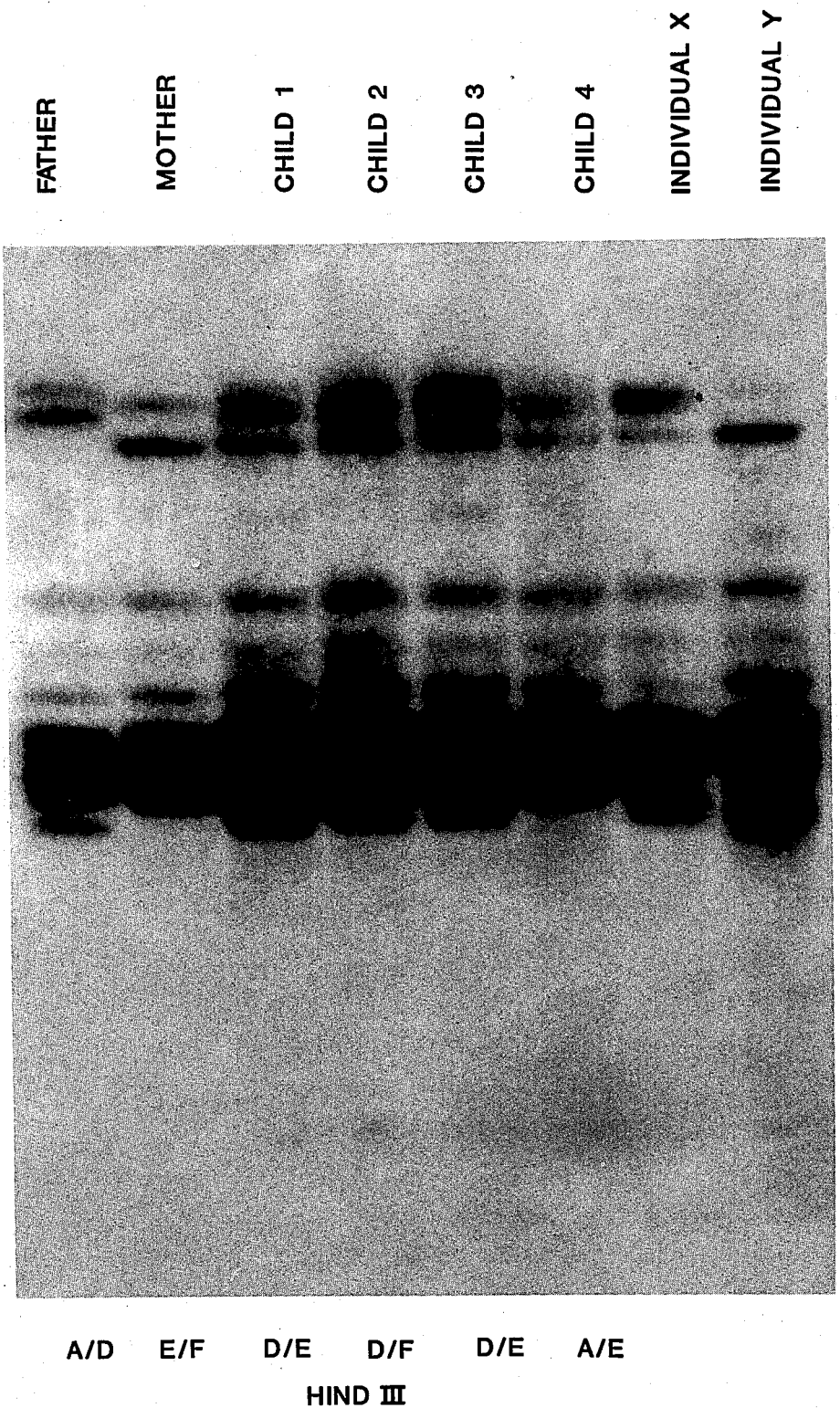
FIGS. 5, 6, and 7 are the autoradiographs described in Example 8.
Figure 6:
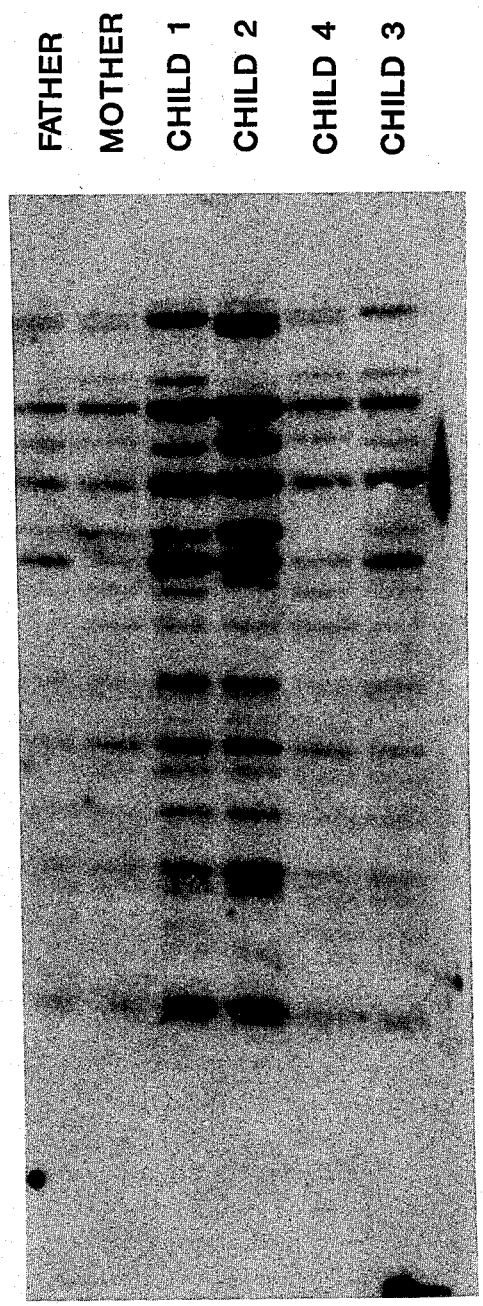
Figure 7:
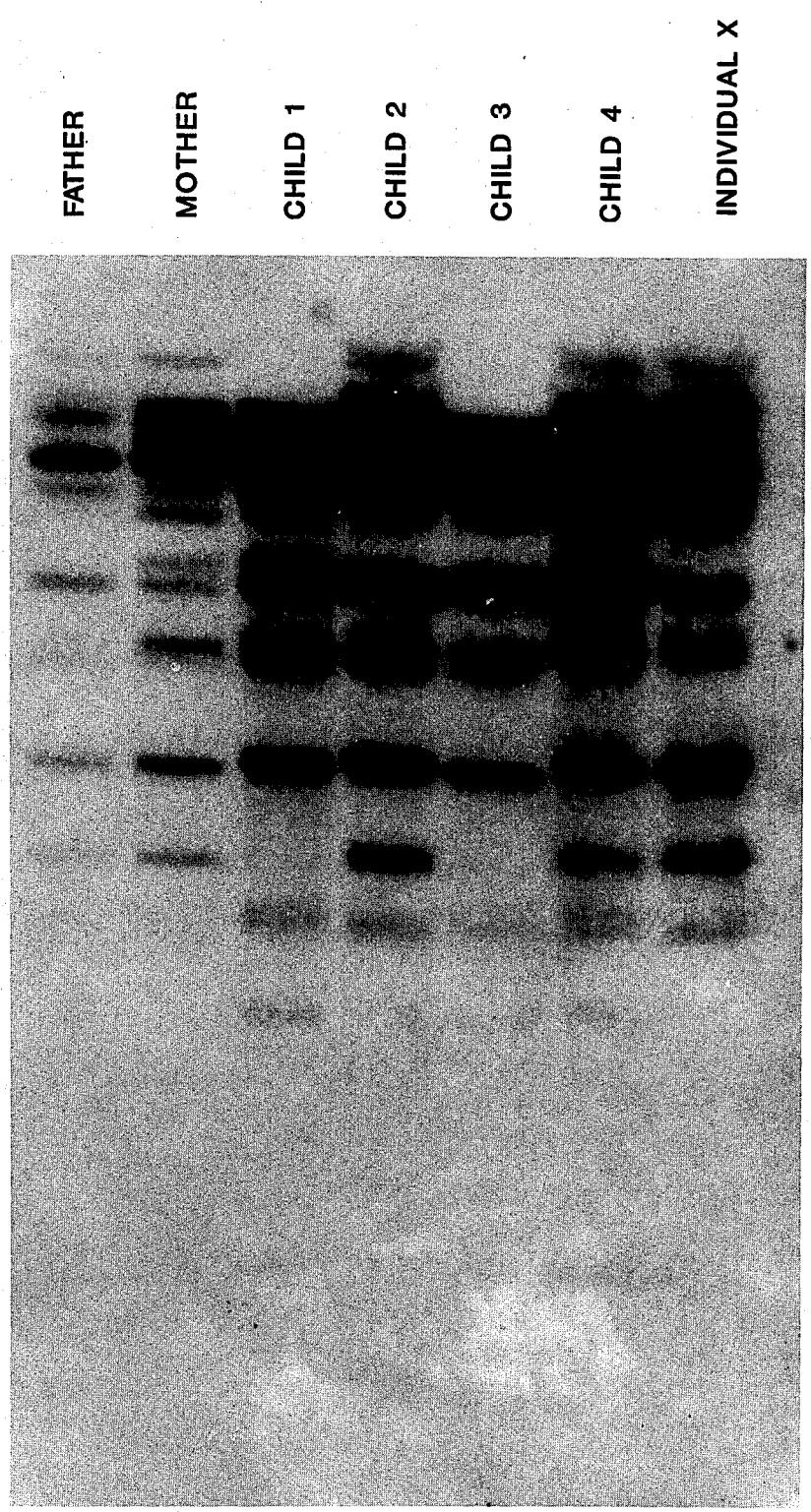

DNA samples from the father, mother, and four children of an HLA typed family and in two instances DNA from one or two individuals (designated X and Y) unrelated to that family were digested according to Example 4 with either HindIII, PvuII, or BamH1. Genomic blots of the digests were made as in Example 4 using the $^{32}$P nick translated HLA-B7 clone as a hybridization probe. FIGS. 5, 6 and 7 are copies of the resulting autoradiographs. The father's haplotype is designated A/D and the mother's haplotype is designated E/F. These autoradiographs indicate that the probe is a multilocus probe that hybridizes to more than one HLA locus. Nonetheless, several polymorphic bands, segregating in the pedigree, are present for each enzyme used. Moreover, the bands segregate with the serologically defined HLA loci so that given fragments may be assigned to an individual chromosome.

Exclusionary paternity determinations may be made using autoradiographs such as FIGS. 5, 6 and 7. An exclusionary pattern would involve a restriction fragment pattern which could not be inherited from the mother and the alleged father. Such a pattern would be one in which the child has a fragment that neither the mother nor alleged father has. Positive paternity determinations using RFLPs will depend upon the frequency of the RFLPs in the general population. In such determinations one calculates the probability that the putative father contributed the RFLP that is observed and compares it with the probability that any random male would contribute the RFLP to the child.

EXAMPLE 9

Use of BglII and HLA-Dp34 (DRα) Probe to Evaluate Linkage and Association Between HLA-DRα and Insulin Dependent Diabetes Mellitus (IDDM) in Six Families Ten μg samples of DNA from the individuals of six different families having histories of IDDM were digested with BglII, blotted, and hybridized with the HLA-Dp34 probe by the procedure of Example 4. Autoradiographs of the resulting genomic blotting patterns were made.

Figure 8:
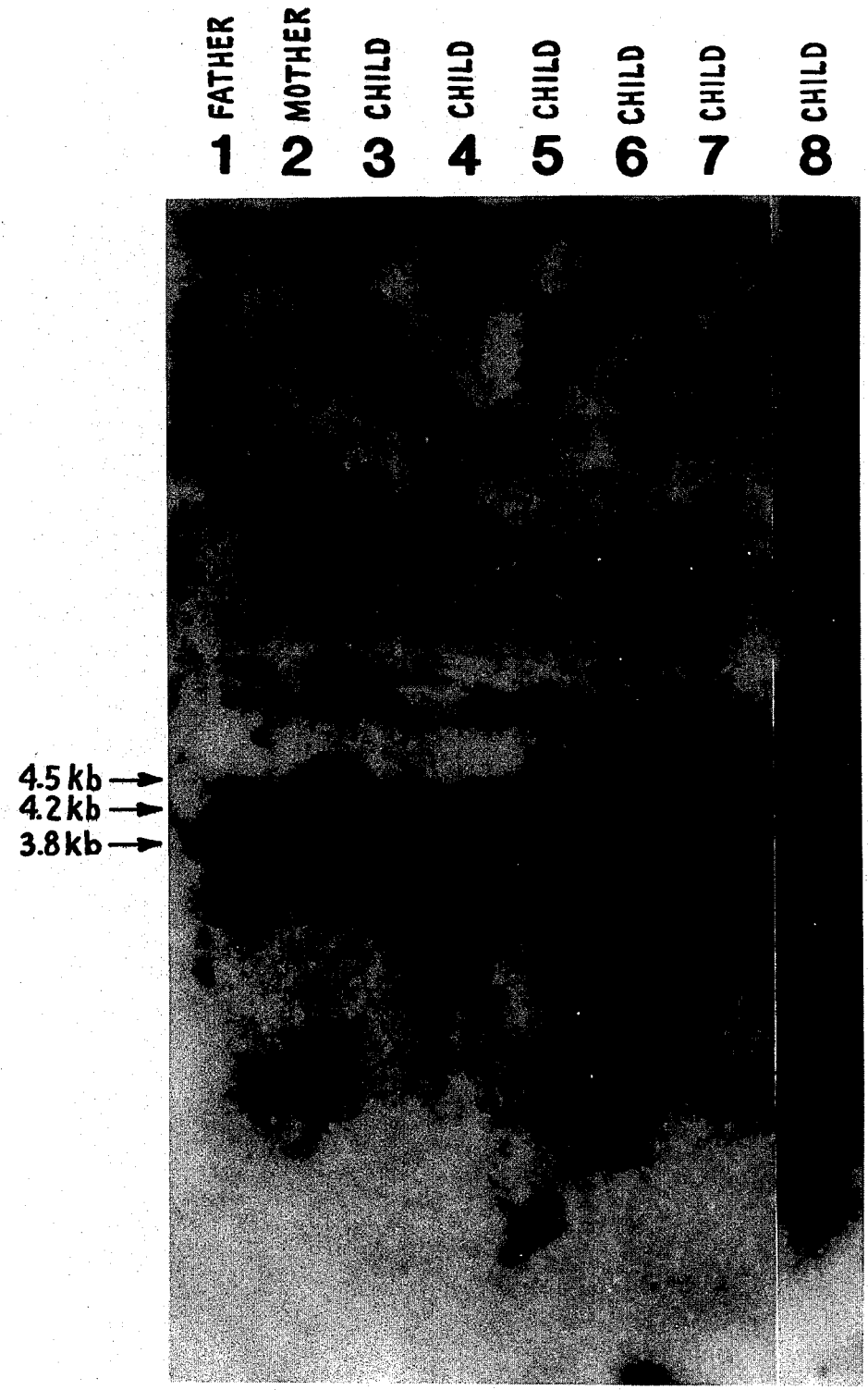
FIGS. 8 and 9 are the autoradiographs described in Example 9.

FIG. 8 is an autoradiograph of eight individuals of one of the families. The father's pattern appears in Lane 1, the mother's in Lane 2 and six children in Lanes 3-8. The father has the 4.2 kb fragment (derived from chromosome 6 haplotype A) and the 3.8 kb fragment from haplotype B. The mother has the 4.2 kb fragment (haplotype C) and the 4.5 kb fragment (haplotype D). The three affected (IDDM) children have either two copies of the 4.2 kb fragment (haplotype A/C, Lanes 3 and 5) or one copy of the 4.2 kb fragments (haplotype A) and one copy of the 4.5 kb fragment (haplotype D) in Lane 4. One unaffected child (Lane 7) has two copies of the 4.2 kb fragment (haplotype A/C). The two unaffected children (Lanes 6 and 8) both have the 3.8 kb fragment (haplotype B) and the 4.5 kb fragment (haplotype D). Thus, the 4.2 kb fragment is linked in this family to a disease susceptibility gene for IDDM. Three of the four children with the 4.2 kb fragment exhibit IDDM, indicating an incomplete penetrance (genetic predisposition) of the disease allele.

In four of the other five families tested the segregation pattern was consistent with linkage of the 4.2 kb BglII fragment to the IDDM disease susceptibility allele.

Figure 9:
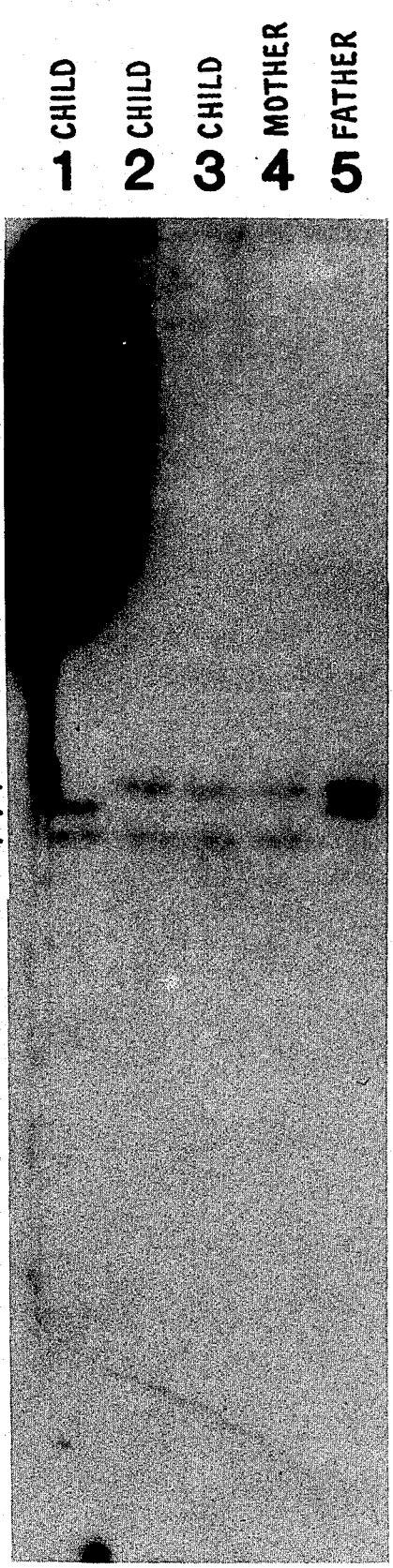

FIG. 9 is an autoradiograph of five individuals of the sixth family. The father's pattern appears in Lane 5, the mother's in Lane 4 and the three children in Lanes 1-3. In this family, disease susceptibility appeared to be linked to the 4.5 kb BglII fragment. Here, the affected father has a 4.5 kb fragment (haplotype A) and 4.2 kb fragment (haplotype B) and the mother has a 4.5 kb fragment (haplotype D) and a 3.8 kb fragment (Haplotype C). Of the three children, only one has IDDM (Lane 3) and he inherited the 4.5 kb fragment from the father and the 3.8 kb fragment from the mother. Therefore, in this family the 4.5 kb BglII fragment is linked to the disease susceptibility allele on the paternal haplotype A.

In summary, five of the six probands in this set of diabetes families had at least one copy of the 4.2 kb BglII fragment. In a sample of unrelated control individuals, 4/16 individual DNA samples had the 4.2 kb fragment, suggesting an increased relative risk (RR) for IDDM associated with the 4.2 kb fragment due, presumably, to linkage disequilibrium between the polymorphic BglII site and a linked IDDM susceptibility allele.

$$RR \text{ (relative risk)} = \frac{(.834) \times (.75)}{(.25)(.167)} = 14$$

By comparison, the relative risk for the serologically defined HLA-DR3=3.3 and for HLA-DR4=6.4. By using more restriction endonucleases and more probes, it should be possible to generate a significantly higher value than the one indicated by these data with the HLA-DRα probe and BglII.

Modifications of the methods and compositions described above that are obvious to those of ordinary skill in genetic engineering, genetics, molecular biology, biochemistry, and/or immunology are intended to be within the scope of the following claims.

I claim:

1. An HLA typing method based on HLA DNA restriction fragment length polymorphism comprising:
   (a) digesting genomic HLA DNA from an individual with a restriction endonuclease that produces a polymorphic digestion pattern of a class II HLA DNA locus;
   (b) subjecting the digest of (a) to genomic blotting using a labeled cDNA that is complementary to a class II HLA DNA locus sequence involved in the polymorphism; and
   (c) comparing the genomic blotting pattern obtained in (b) with a standard genomic blotting pattern for said HLA DNA sequence obtained using said restriction endonuclease and an equivalent labeled cDNA probe.

2. The method of claim 1 wherein the locus is the DRα locus, a DRα related locus, or the DRβ locus.

3. The method of claim 1 wherein:
   (i) the locus is the DRα locus and the restriction endonuclease is BglII or EcoRV, or
   (ii) the locus is a DR? related locus and the restriction endonuclease is BglII, or
   (iii) the locus is the DR? locus or a DR? related locus and the restriction endonuclease is EcoRI or BglII.

4. A method of determining whether an individual is susceptible to a disease comprising:
   (a) digesting genomic HLA DNA from the individual with a restriction endonuclease that produces a polymorphic digestion pattern of a class II HLA locus that is associated with the disease;
   (b) subjecting the digest of (a) to genomic blotting using a labeled cDNA probe that is complementary to the DNA sequence of said class II HLA locus;
   (c) comparing the genomic blotting pattern obtained in (b) with a standard genomic blotting pattern of an individual having said disease obtained using said restriction endonuclease and an equivalent labeled cDNA probe.

5. The method of claim 4 wherein said locus is the DRα locus.

6. The method of claim 5 wherein the restriction endonuclease is BglII.

7. A method for determining the paternity of an individual based on HLA DNA restriction fragment length polymorphism comprising:
  (a) digesting genomic HLA DNA of the mother of the individual, the suspected father of the individual, and the individual with a restriction endonuclease that produces a polymorphic digestion pattern of a class II HLA DNA locus;
  (b) subjecting each of the digests of (a) to genomic blotting using a labeled cDNA probe that is complementary to a class II HLA DNA sequence involved in the polymorphism; and
  (c) comparing the genomic blotting patterns obtained in (b) to determine correspondence between the individual's pattern and the mother's pattern and suspected father's pattern and thereby determining whether the suspected faster is the actual father of the individual.

8. A method for determining transplant or transfusion compatibility based on HLA DNA restriction fragment length polymorphism comprising:
  (a) digesting genomic HLA DNA of the transplant or transfusion donor and the transplant or transfusion host with a restriction endonuclease that produces a polymorphic digestion pattern of a class II HLA DNA locus;
  (b) subjecting each of the digests of (a) to genomic blotting using a labeled cDNA probe that is complementary to a class II HLA DNA sequence involved in the polymorphism; and
  (c) comparing the genomic blotting patterns obtained in (b) to determine correspondence therebetween and thereby determining whether the transplant or transfusion donor's HLA is compatible with the transplant or transfusion host's HLA.

9. An HLA typing method based on HLA DNA restriction fragment length polymorphism comprising:
  (a) digesting genomic HLA DNA from an individual with a restriction endonuclease that produces a polymorphic digestion pattern of a class II HLA DNA;
  (b) solution hybridizing the digest of step (a) with a labeled cDNA probe that is complementary to a class II HLA DNA sequence involved in the polymorphism;
  (c) resolving the hybridizate of step (b);
  (d) detecting labeled hybrids in the resolved hybridizate; and
  (e) comparing the resolution pattern of the labeled hybrids with a standard resolution pattern for said HLA DNA sequence obtained using the restriction endonuclease and an equivalent labeled cDNA probe.

* * * * *